(12) United States Patent
Schässburger et al.

(10) Patent No.: US 12,369,894 B2
(45) Date of Patent: Jul. 29, 2025

(54) BIOPSY ARRANGEMENT

(71) Applicant: NeoNavia AB, Vallentuna (SE)

(72) Inventors: Kai-Uwe Schässburger, Lidingö (SE); Magnus Olsen, Vallentuna (SE); Anna Foghelin, Stockholm (SE); Jörgen Vrenning, Lidingö (SE); Anna Eriksrud, Stocksund (SE); Ronny Ståhle, Växjö (SE); Lars-Peter Svanberg, Stockholm (SE)

(73) Assignee: NeoNavia AB, Vallentuna (SE)

( * ) Notice: Subject to any disclaimer, the term of this patent is extended or adjusted under 35 U.S.C. 154(b) by 1065 days.

(21) Appl. No.: 17/272,983

(22) PCT Filed: Aug. 30, 2019

(86) PCT No.: PCT/EP2019/073208
§ 371 (c)(1),
(2) Date: Mar. 3, 2021

(87) PCT Pub. No.: WO2020/048888
PCT Pub. Date: Mar. 12, 2020

(65) Prior Publication Data
US 2022/0211358 A1 Jul. 7, 2022

(30) Foreign Application Priority Data
Sep. 3, 2018 (EP) .................................. 18192314

(51) Int. Cl.
*A61B 10/02* (2006.01)
*A61B 90/90* (2016.01)
*A61B 17/00* (2006.01)

(52) U.S. Cl.
CPC ...... *A61B 10/0283* (2013.01); *A61B 10/0266* (2013.01); *A61B 90/90* (2016.02);
(Continued)

(58) Field of Classification Search
None
See application file for complete search history.

(56) References Cited

U.S. PATENT DOCUMENTS

| 5,121,751 A | 6/1992 | Panalletta |
| 5,188,118 A | 2/1993 | Terwilliger |

(Continued)

FOREIGN PATENT DOCUMENTS

| DE | 20211934 U1 | 11/2002 |
| EP | 1832234 A2 | 9/2007 |

(Continued)

*Primary Examiner* — Matthew Kremer
(74) *Attorney, Agent, or Firm* — Renner, Otto, Boisselle & Sklar, LLP

(57) ABSTRACT

A biopsy arrangement for taking a biopsy in a human or animal tissue, said biopsy arrangement comprising: a driver unit; and at least two different types of probes which can be releasably connected to the driver unit, said at least two different types of probes comprising at least a first probe type and a second probe type, wherein said driver unit comprises at least two different probe controlling devices which are controlling different probe modules in a connected probe, said at least two different probe controlling devices comprising a suction generating device and a needle moving device, and wherein probe modules of the first probe type comprise a suction transferring module and at least one needle manipulating module, wherein said suction transferring module is configured for transferring a suction from the suction generating device of the driver unit to a needle of the first probe type and wherein said at least one needle manipulating module is a first probe type needle manipulating module configured for providing longitudinal and/or rotational movement to at least a part of the needle of the first probe type, and wherein probe modules of the second probe type comprise at least one needle manipulating module, which is a second probe type spring loaded needle manipu-
(Continued)

lating module which is configured for providing a spring loaded longitudinal movement to at least a part of a needle of the second probe type.

9 Claims, 6 Drawing Sheets

(52) U.S. Cl.
 CPC ......... *A61B 2010/0208* (2013.01); *A61B 2010/0225* (2013.01); *A61B 2017/00464* (2013.01)

(56) References Cited

U.S. PATENT DOCUMENTS

| | | | |
|---|---|---|---|
| 5,348,022 A | 9/1994 | Leigh et al. | |
| 5,392,790 A | 2/1995 | Kanner et al. | |
| 5,615,690 A | 4/1997 | Giurtino et al. | |
| 6,120,463 A | 9/2000 | Bauer | |
| 7,828,748 B2 | 11/2010 | Hibner | |
| 8,282,573 B2 | 10/2012 | Shabaz et al. | |
| 8,313,444 B2 | 11/2012 | Thompson et al. | |
| 2007/0032741 A1 | 2/2007 | Hibner et al. | |
| 2008/0071193 A1* | 3/2008 | Reuber | A61B 10/0096 600/567 |
| 2008/0228103 A1 | 9/2008 | Ritchie et al. | |
| 2009/0012423 A1 | 1/2009 | Peters | |
| 2009/0131819 A1* | 5/2009 | Ritchie | A61B 10/0275 600/564 |
| 2010/0160816 A1* | 6/2010 | Parihar | A61B 10/0096 600/564 |
| 2011/0208088 A1 | 8/2011 | Leimbach et al. | |
| 2012/0029354 A1 | 2/2012 | Mark et al. | |
| 2012/0265095 A1* | 10/2012 | Fiebig | A61B 10/0275 600/567 |
| 2012/0283563 A1* | 11/2012 | Moore | A61B 8/463 600/437 |
| 2013/0150751 A1 | 6/2013 | Fiebig et al. | |
| 2013/0267869 A1 | 10/2013 | Speeg et al. | |
| 2015/0065913 A1* | 3/2015 | Keller | A61B 10/0283 600/566 |

FOREIGN PATENT DOCUMENTS

| | | |
|---|---|---|
| EP | 2323563 | 5/2011 |
| EP | 2520237 | 11/2012 |
| EP | 3206587 | 8/2017 |
| RU | 2212848 C2 | 9/2003 |
| WO | 2000010465 | 3/2000 |
| WO | 0056220 | 9/2000 |
| WO | 2005063126 | 7/2005 |
| WO | 2008076712 A2 | 6/2008 |
| WO | 2008115526 | 9/2008 |
| WO | 2012015801 | 2/2012 |
| WO | 2014007380 | 1/2014 |
| WO | 2016058845 | 4/2016 |

\* cited by examiner

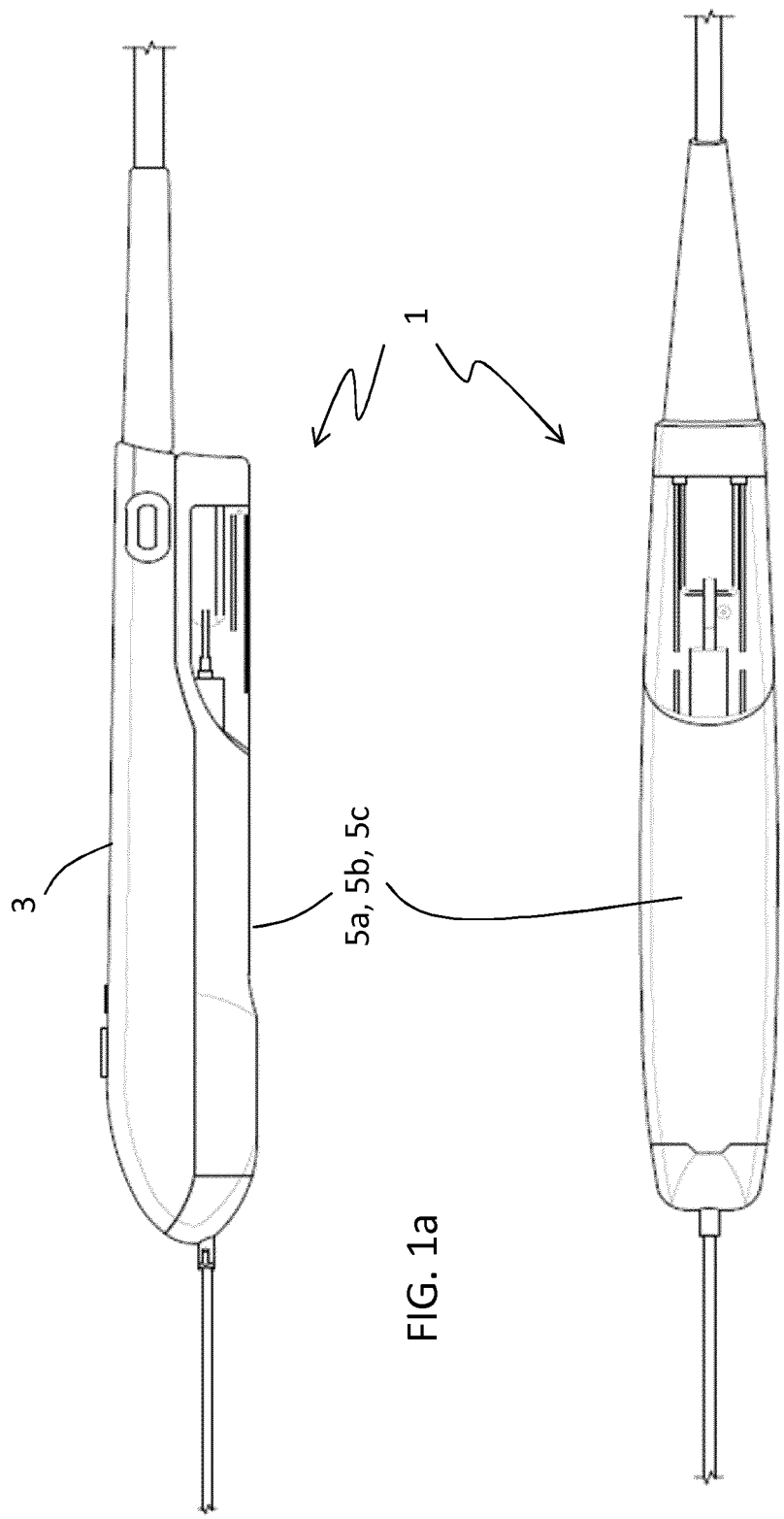

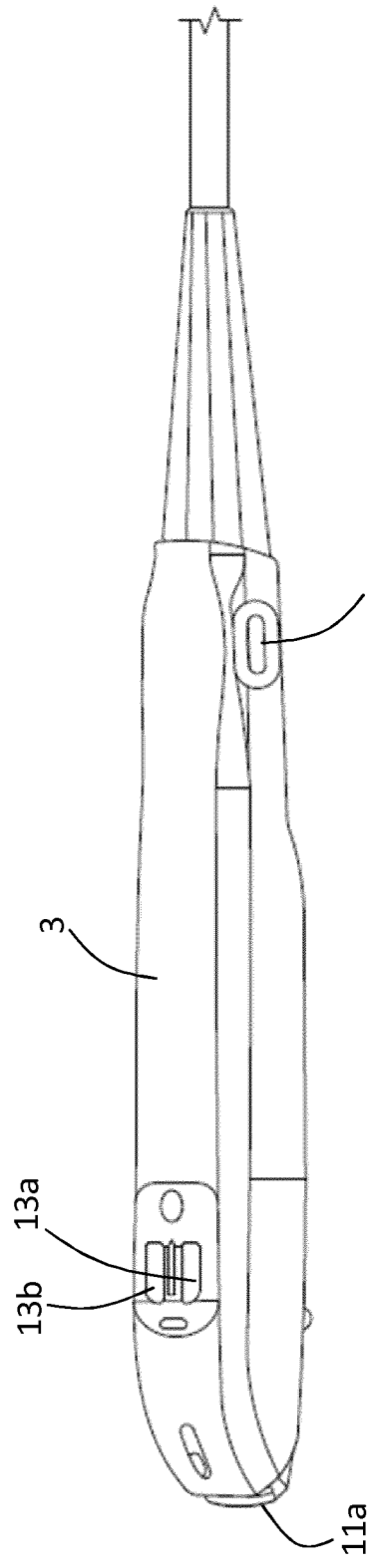
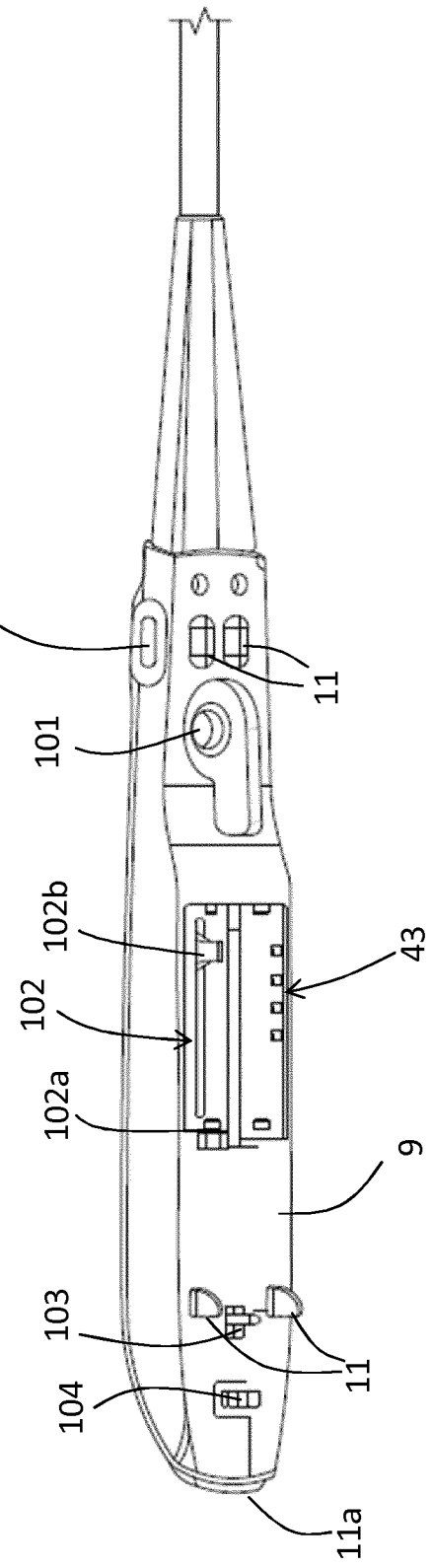
FIG. 2a
FIG. 2b

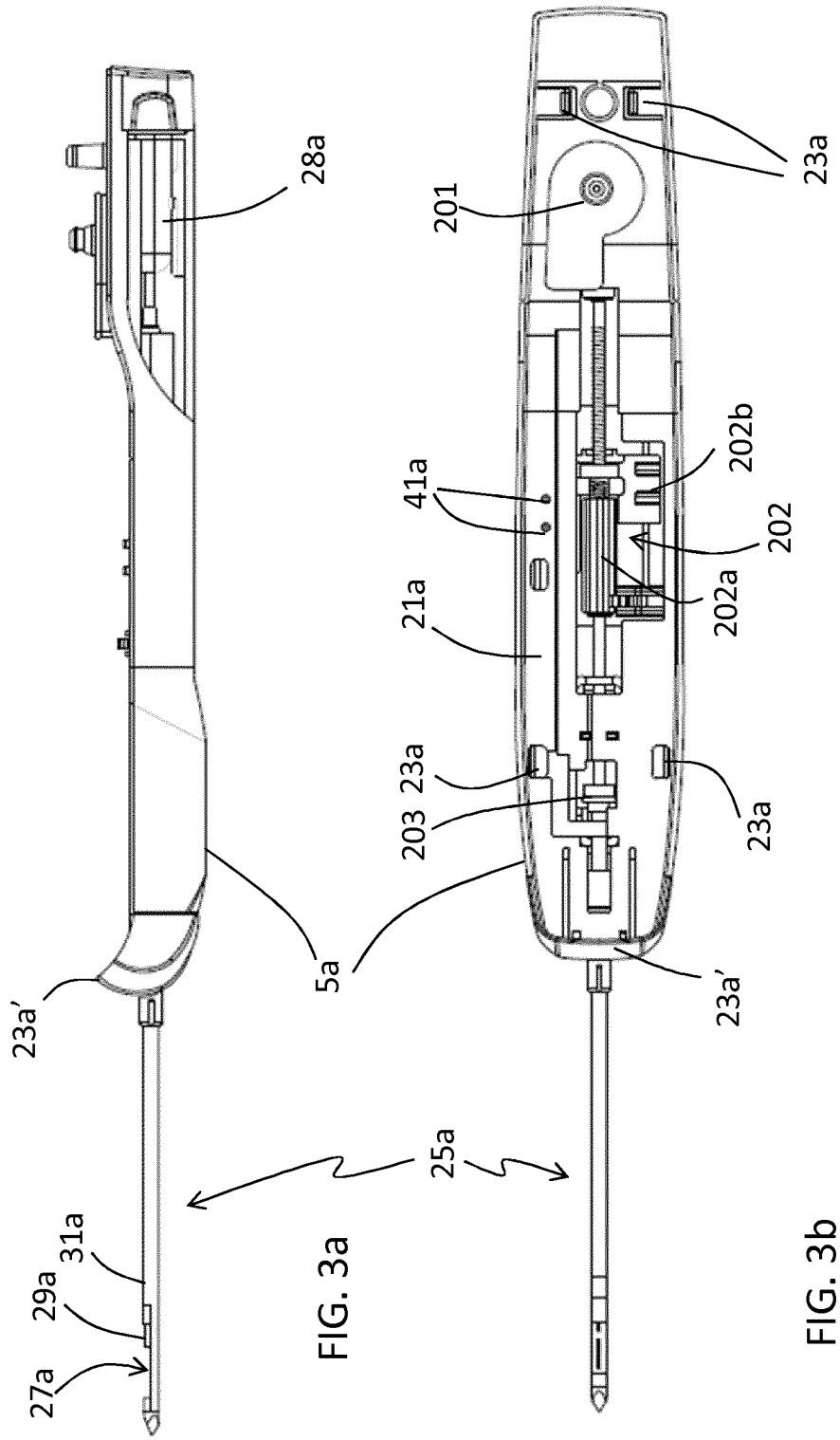

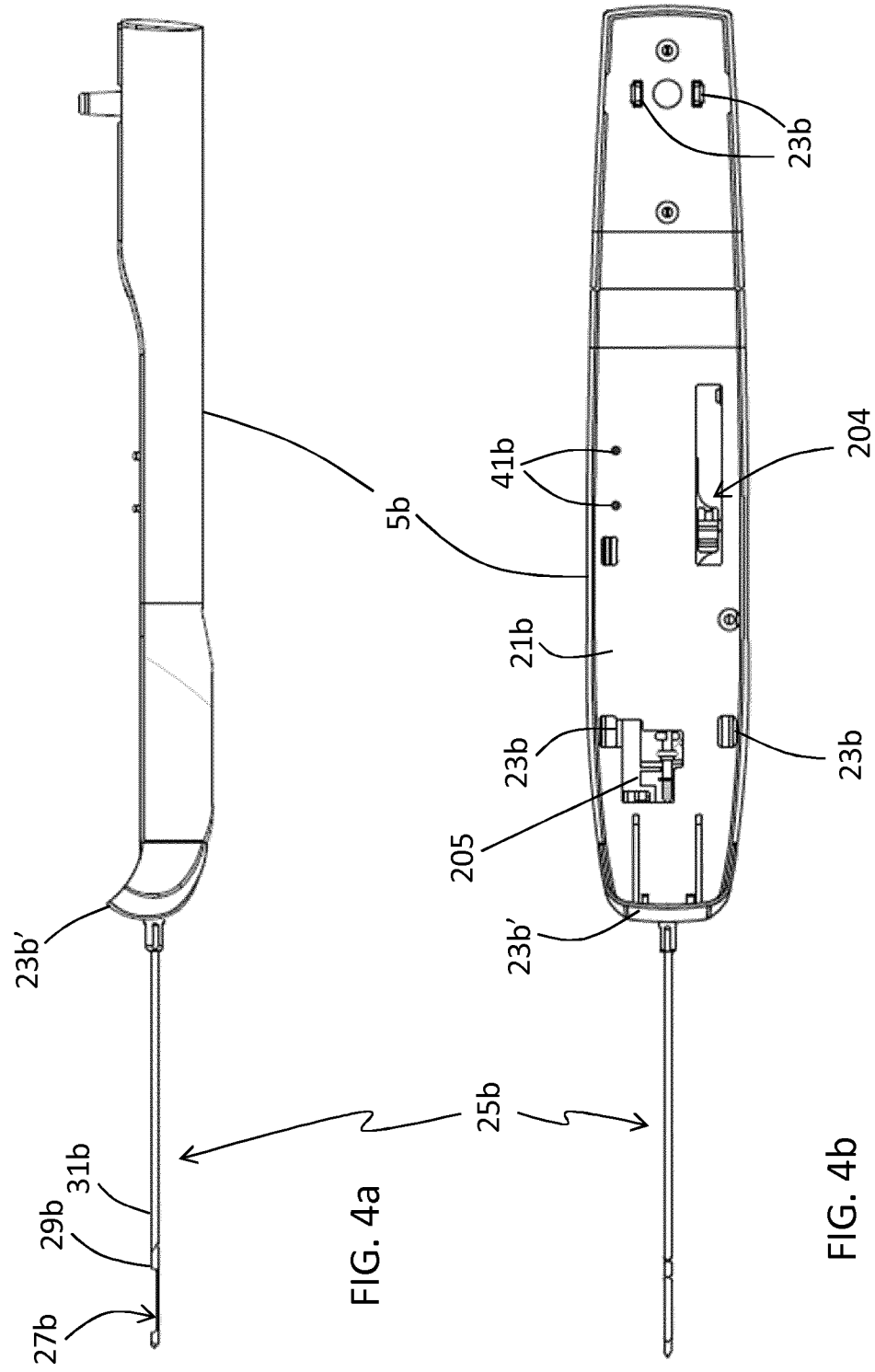

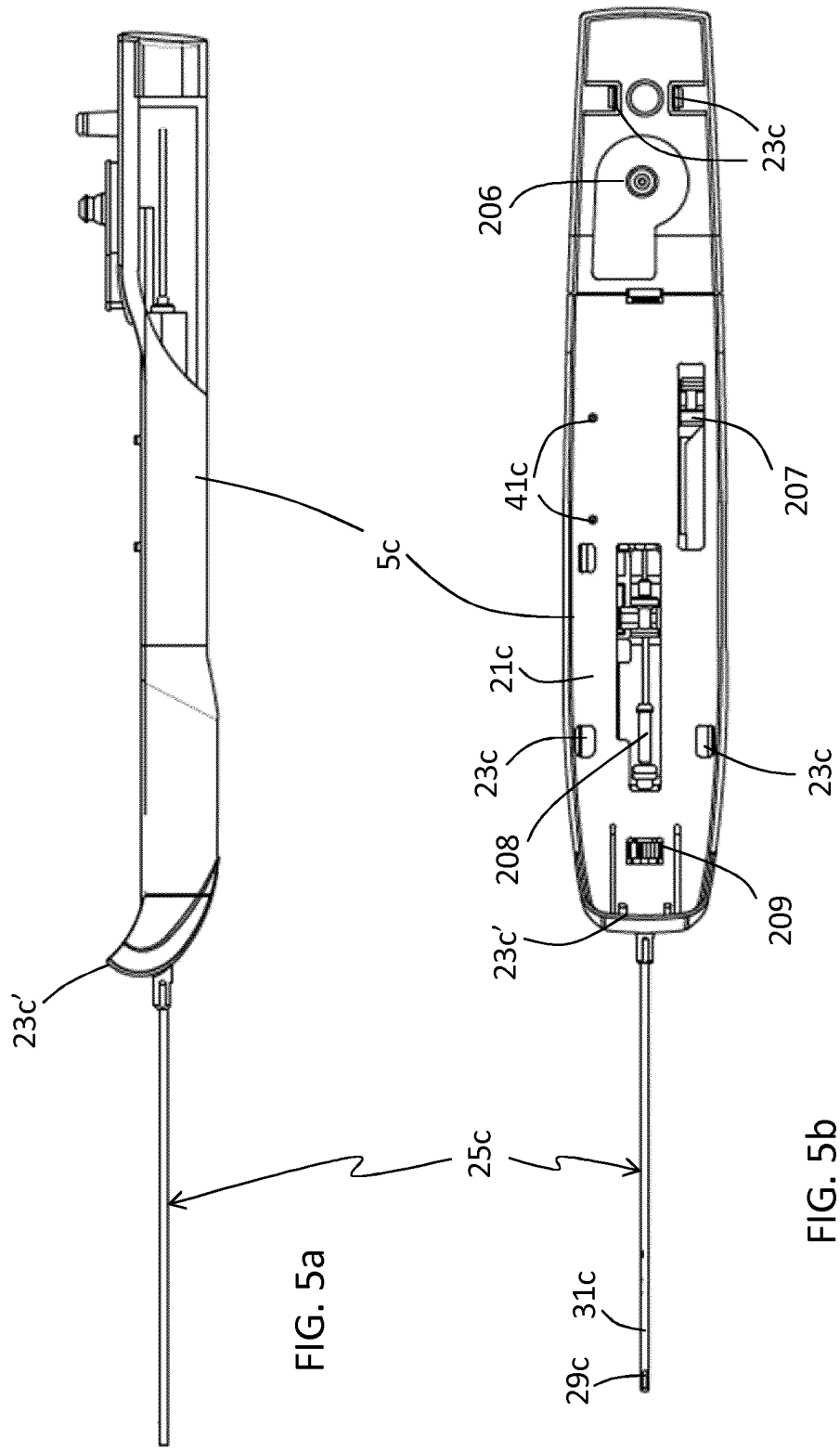

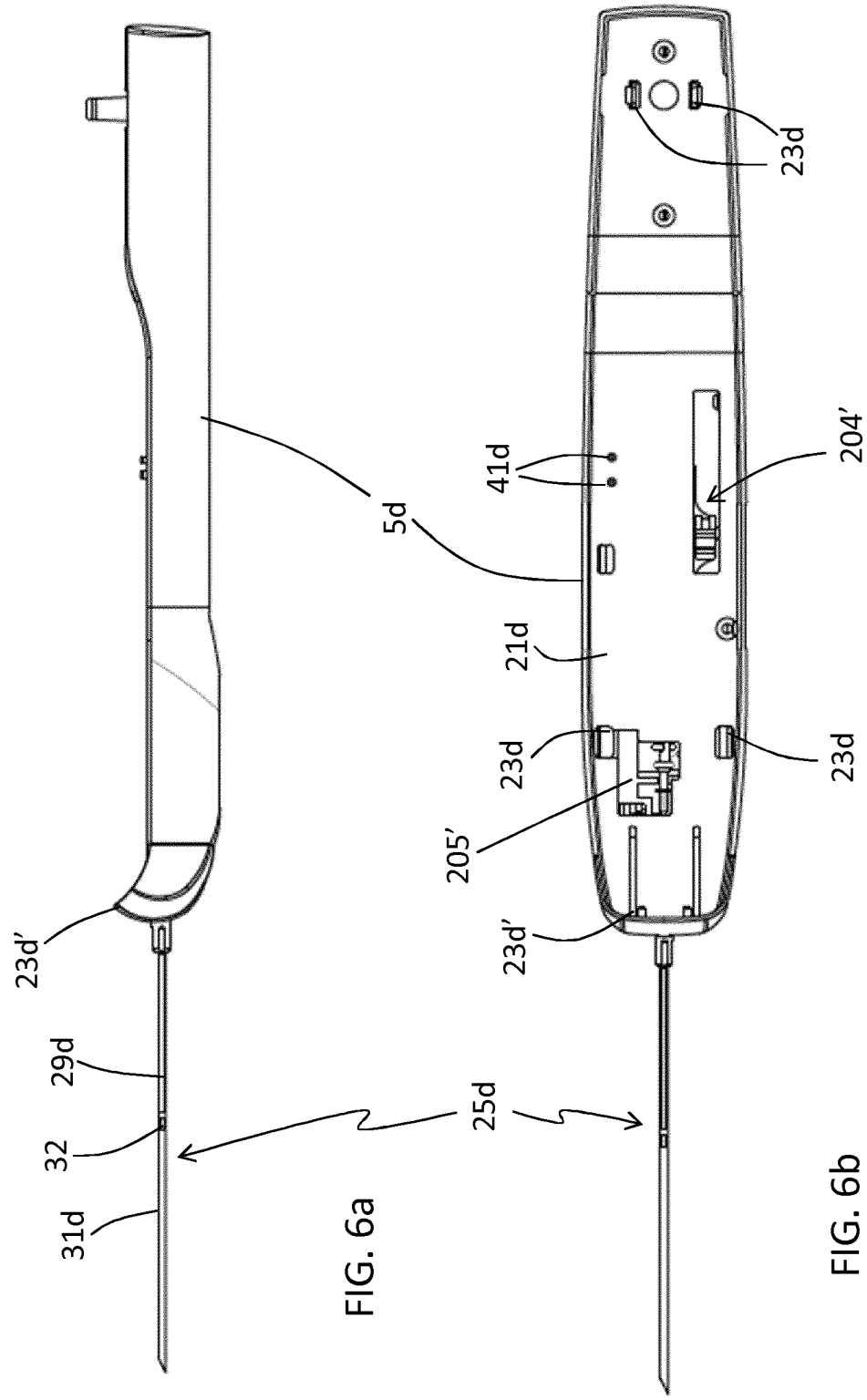

BIOPSY ARRANGEMENT

This application is a national phase of International Application No. PCT/EP2019/073208 filed Aug. 30, 2019 and published in the English language, which claims priority to European Application No. 18192314.5 filed Sep. 3, 2018, both of which are hereby incorporated herein by reference.

TECHNICAL FIELD OF THE INVENTION

The present invention relates to a biopsy arrangement for taking a biopsy in a human or animal tissue, a driver unit and probes.

BACKGROUND OF THE INVENTION

Today it is generally accepted that the final diagnosis of malignant suspicious lesions has to be confirmed using biopsy techniques. The most commonly performed cell- and tissue-sampling techniques are fine needle aspiration (FNA) using mainly 22G and 23G needles (0.6-0.7 mm in diameter) and core needle biopsy (CNB) or vacuum assisted biopsy (VAB) needles using everything between 8G and 18G needles (1.3-4.2 mm in diameter), with the latter two techniques dominating globally. Because of the significantly improved sensitivity and minimally invasiveness when combining needle biopsy techniques with imaging guidance the number of open surgical biopsies is steadily declining.

In contrast to FNA, CNB and VAB allow for large volume tissue sampling which permits differentiation between in situ and invasive lesions, histologic diagnosis of micro-calcifications and the analysis of several relevant biomarkers.

There are significant advancements when it comes to visualization techniques continuously pushing the boundaries for what is possible when it comes to locating a suspicious lesion. In addition a number of developments like the use of advanced biomarkers for following and personalizing adjuvant treatment are defining new requirements concerning very precise and minimally invasive tissue sampling.

The distal end of biopsy needles used in most CNB and VAB devices is a sharp, solid tip, which is needed for penetration of tissue towards the location where a biopsy is to be taken. To penetrate suspicious lesions the needle has to be inserted manually or using the generally used spring-loaded mechanism to thrust the needle into the lesions with a predetermined length. Thereafter a tissue sampling procedure is initiated, usually incorporating the opening of a residual space which is filled with surrounding tissue and subsequently closed, whereby the tissue inside the residual space is severed from surrounding tissue.

The opening and possible closing of the residual space is usually accomplished by the relative movement of two separate elements of the needle biopsy assembly, e.g. an inner sampling needle relative to an outer cutting needle, an inner trocar relative to an outer sampling needle, or a distal cutting blade relative to a distal tip sampling needle.

Different types of biopsy devices are well known in the art. A few documents describing biopsy devices with hollow needles and elongated rods are WO 0056220, EP 2520237, US 2012/0029354, U.S. Pat. Nos. 5,188,118, 5,348,022, 5,121,751, 6,120,463, 8,282,573, 7,828,748, WO 2014/007380, DE 20211934U, U.S. Pat. Nos. 8,313,444, and 5,392,790. A core biopsy arrangement has been described by the present applicant in EP 2323563, wherein a reciprocating longitudinal movement is applied to a biopsy needle. In EP 3206587 and WO 2016/058845 the present applicant discloses a biopsy arrangement utilizing such a reciprocating longitudinal movement of the biopsy needle where specific details around the needle configuration comprising an inner trocar and a specific configuration of the needle distal tip for cutting the sample is described. Further, the following documents describe biopsy arrangements comprising blades or severing arrangements: WO 2012015801, EP 1832234, WO 0010465, U.S. Pat. No. 5,615,690, RU 2212848, US 2009012423, WO 2008115526.

Additionally, the manual insertion of large diameter needles through healthy tissue towards the targeted lesion can be cumbersome, especially if said tissue is dense or fibrotic. The physician has to apply manual force to navigate the needle towards the lesion while maintaining dexterity and control not to injure vessels and organs. The insertion process is a source of patient anxiety and should therefore be as short and efficient as possible.

The cases indicated for biopsy vary widely in technical complexity regarding location and size of the lesion as well as the need for tissue volume. Different devices with different needle insertion and sample acquisition mechanism are used dependent on the requirements of the case at hand.

This requires the physician to be trained in the use of several different biopsy platforms. Ultrasound-guided biopsies are highly dependent on the experience of the physician. The need for multiple biopsy platforms limits the experience a physician can gain on each single platform. The healthcare facility needs to purchase, store and maintain multiple biopsy platforms with obvious economic disadvantages.

SUMMARY

An object of the present invention is to provide a biopsy arrangement which can be used for taking a biopsy from many different types of lesions in different locations.

A further object of the present invention is to provide a biopsy arrangement with improved flexibility and unprecedented ease of use.

This is achieved by a biopsy arrangement, a driver unit and a probe according to the independent claims.

According to one aspect of the invention a biopsy arrangement for taking a biopsy in a human or animal tissue is provided. Said biopsy arrangement comprises:
- a driver unit; and
- at least two different types of probes which can be releasably connected to the driver unit, said at least two different types of probes comprising at least a first probe type and a second probe type,
- wherein said driver unit comprises at least two different probe controlling devices which are controlling different probe modules in a connected probe, said at least two different probe controlling devices comprising a suction generating device and a needle moving device, and
- wherein probe modules of the first probe type comprise a suction transferring module and at least one needle manipulating module, wherein said suction transferring module is configured for transferring a suction from the suction generating device of the driver unit to a needle of the first probe type and wherein said at least one needle manipulating module is a first probe type needle manipulating module configured for providing longitudinal and/or rotational movement to at least a part of the needle of the first probe type, and
- wherein probe modules of the second probe type comprise at least one needle manipulating module, which is a second probe type spring loaded needle manipulating module which is configured for providing a spring loaded longitudinal movement to at least a part of a needle of the second probe type,
wherein the different types of probes use different sampling techniques.

According to another aspect of the invention a driver unit for use together with at least two different types of probes for taking a biopsy in a human or animal tissue is provided. Said driver unit comprises a first connection device for releasably connecting said probes, wherein said driver unit comprises at least two different probe controlling devices which can control different probe modules in a connected probe, wherein the different types of probes use different sampling techniques.

According to another aspect of the invention a probe for taking a biopsy or leaving a marker in a human or animal tissue is provided, which probe comprises a second connection device configured for releasable connection to a first connection device of a driver unit as described above, wherein said probe comprises at least one needle manipulating module.

Hereby a biopsy arrangement is provided where a driver unit can be used for a number of different types of probes. The driver unit can hereby be reused and the probes can suitably be single use probes. Different types of probes are in this invention not only different dimensions of the biopsy needles but also includes different means for sampling the tissue which also requires different functions for controlling the probe. At least one of the probe types which can be connected to and controlled by the driver unit comprises a suction transferring module and at least one of the probe types comprises a spring loaded needle manipulating module. Hereby both core needle biopsy and vacuum assisted biopsy can be provided by one and the same biopsy arrangement. The driver unit comprises at least two different probe controlling devices comprising a suction generating device and a needle moving device. Probe modules in the different probes can be controlled by the probe controlling devices in the driver unit when the probes are connected to the driver unit. Hereby the physician can easily change between different probe types and still use the same driver unit. A user friendly device is provided since the interface is extremely simplistic and physicians only need to master one driver unit. The most suitable probe type can be chosen for each patient and for each lesion which strongly facilitates the work given the heterogeneity of lesions sampled today (small, large, soft, hard, difficult locations etc.). Modern visualization techniques enables targeting smaller and smaller lesions and changes in treatment regimes are adding requirements for repeat biopsies during neoadjuvant treatment as well as pre-operative sampling of lymph nodes. The simplified procedure and the flexibility of the biopsy arrangement results in that tissue samples of better quality can be taken, which supports the important development of personalized medicine. Furthermore with a biopsy arrangement according to the invention the situation for the physician (typically a radiologist) will be improved and it will facilitate for more inexperienced users to manage complex cases with ease. This will increase operational efficiency of healthcare facilities. With a biopsy arrangement according to the invention clinics would only need one biopsy platform instead of a number of different platforms used for different types and positions of tumors. The high quality of the tissue samples provided by the biopsy arrangement according to the invention will improve possibility for both correct diagnosis and treatment.

In one embodiment of the invention said suction generating device of the driver unit is configured for connecting to a suction transferring module of a connected probe and said needle moving device of the driver unit is configured for connecting to one or more needle manipulating modules of a connected probe for controlling longitudinal and/or rotational movement of at least a part of a needle of a probe connected to the driver unit.

In one embodiment of the invention said probe controlling devices of the driver unit further comprise a pulsing device which can transfer reciprocating pulses to a needle of a connected probe. Hereby longitudinal, reciprocating pulses can be transferred to a biopsy needle of a connected probe. Such a reciprocating oscillating movement of the needle or a part of the needle (inner needle part and/or outer needle part, such as cannulas or trocars) is especially suitable when dense or fibrotic tissue need to be penetrated on the way to a tumor. Also when penetrating the tumor for taking a biopsy the oscillating movement can preferably be used in order to improve the filling of the needle with tissue utilizing the inertia stabilization caused by the fast acceleration pulses applied to the needle.

In one embodiment of the invention a further probe module of both the first and second probe types is a pulse transferring module which is configured for transferring reciprocating pulses provided from the pulsing device of the driver unit to at least a part of a needle of the first and second probe types when connected to the driver unit.

In one embodiment of the invention the pulse transferring module of at least one of the different types of probes is configured for transferring reciprocating pulses provided from the pulsing device of the driver unit to both an inner and an outer needle part of a needle of the probe and the pulse transferring module of another one of the different types of probes is configured for transferring reciprocating pulses provided from the pulsing device of the driver unit to only one of an inner and an outer needle part of the needle.

In one embodiment of the invention said biopsy arrangement comprises a third probe type which can be releasably connected to the driver unit, said third probe type being a different type of probe than the first and the second probe types, wherein probe modules of the third probe type comprise a suction transferring module and a needle manipulating module, wherein said suction transferring module is configured for transferring a suction from the suction generating device of the driver unit to a needle of the third probe type and wherein said needle manipulating module is a third probe type needle manipulating module, which is configured for providing longitudinal movement to an inner needle part of the needle of the third probe type for positioning of the inner needle part in a front or back position in relation to an outer needle part of the needle and configured for providing rotational movement to the outer needle part of the needle. Hereby three different probe types using different sampling techniques can be used with one and the same reusable driver unit.

In one embodiment of the invention said third probe type further comprises a sample separating module configured for cooperating with a sample separating device provided in the driver unit, said sample separating device comprising or being connected to a motor, wherein said sample separating module is connected to an outer needle part of the needle such that a rotational movement can be provided to the outer needle part from the sample separating device through the sample separating module.

In one embodiment of the invention said third probe type further comprises a pulse transferring module which is configured for transferring reciprocating pulses provided from the pulsing device of the driver unit to an inner and/or outer needle part of a needle of the third probe type.

In one embodiment of the invention said biopsy arrangement further comprises a fourth probe type which can be releasably connected to the driver unit, wherein said fourth probe type is a marker probe configured for leaving a marker in a human or animal tissue, which marker probe can be controlled by one or more of the probe controlling devices provided in the driver unit. Hereby the biopsy arrangement according to the invention can also be used for leaving a marker in the tissue, i.e. one and the same driver unit can be used also for the marker probe. This will provide an effective and easily handled system.

In one embodiment of the invention at least one of the at least two different types of probes comprises a distal-tip loaded needle and at least one of the at least two different types of probes comprises a side aperture needle. Hereby different probes comprising different needle types, using different sampling techniques can be used with one and the same driver unit.

In one embodiment of the invention each one of the at least two different types of probes comprises a unique probe identification and the driver unit comprises a probe identification recognition device which is connected to the at least two different probe controlling devices and comprises control logic such that the probe identification recognition device can activate certain probe controlling devices in dependence of which type of probe has been identified by the probe identification recognition device. Hereby one and the same driver unit can be used for different probe types and different functions in the driver unit can be activated in dependence of type of probe connected.

Further embodiments of the invention are described in the dependent claims.

BRIEF DESCRIPTION OF THE DRAWINGS

FIG. 1a is a perspective side view and FIG. 1b is a perspective bottom view of a biopsy arrangement according to one embodiment of the invention.

FIG. 2a is a perspective top view and FIG. 2b is a perspective bottom view of a driver unit according to one embodiment of the invention.

FIG. 3a is a side view and FIG. 3b is a bottom view of a first probe type according to one embodiment of the invention.

FIG. 4a is a side view and FIG. 4b is a bottom view of a second probe type according to one embodiment of the invention.

FIG. 5a is a side view and FIG. 5b is a bottom view of a third probe type according to one embodiment of the invention.

FIG. 6a is a side view and FIG. 6b is a bottom view of a fourth probe type according to one embodiment of the invention.

DETAILED DESCRIPTION OF EMBODIMENTS

FIGS. 1a and 1b show different perspective views of a biopsy arrangement 1 according to one embodiment of the invention. The biopsy arrangement 1 is an arrangement for taking a biopsy in a human or animal tissue and comprises according to the invention a driver unit 3 and at least two different types of probes 5a, 5b, 5c, 5d which can be releasably connected to the driver unit 3. The driver unit 3 can suitably be hand held and it is reusable. The probes 5a, 5b, 5c, 5d are suitably single use biopsy probes or a marker probe. The at least two different types of probes comprise at least a first probe type 5a and a second probe type 5b. According to the invention these different types of probes are not only different dimensions of the biopsy needles but also including different functions for controlling the probe. At least one of the single use probe types which can be connected to and controlled by the driver unit comprises a suction transferring module and at least one of the single use probe types comprises a spring loaded needle manipulating module. Hereby both core needle biopsy and vacuum assisted biopsy can be provided by one and the same biopsy arrangement. Hereby the different types of probes use different sampling techniques.

FIGS. 2a and 2b show different perspective views of the driver unit 3 of the biopsy arrangement 1 as shown in FIGS. 1a and 1b. In FIG. 2b a driver connection surface 9 of the driver unit 3 can be seen which driver connection surface 9 can be mated and connected with a probe connection surface 21a, 21b, 21c, 21d of a connected probe 5a, 5b, 5c, 5d. FIGS. 3-6 show four different types of probes 5a, 5b, 5c, 5d according to embodiments of the invention which can be used together with the driver unit 3 as shown in FIG. 2. FIGS. 3a and 3b show a first probe type 5a, FIGS. 4a and 4b show a second probe type 5b, FIGS. 5a and 5b show a third probe type 5c and FIGS. 6a and 6b show a fourth probe type 5d. According to the invention at least two different single use probe types should be provided for connection to one and the same driver unit. All the four probe types 5a, 5b, 5c, 5d as shown in FIGS. 3, 4, 5 and 6 need not be provided according to the invention and furthermore different properties of the different probe types which will be described in detail below with reference to FIGS. 3-6 may be combined differently in different probe types and still be within the scope of the invention.

The driver unit 3 comprises at least two different probe controlling devices 101, 102, 103, 104 which are controlling different probe modules 201, 202, 203, 204, 205, 206, 207, 208, 209 in a connected probe 5a, 5b, 5c, 5d. The at least two different probe controlling devices 101, 102, 103, 104 comprise at least a suction generating device 101 and a needle moving device 102. The needle moving device 102 is a DC motor both directly coupled to a cogwheel 102a generating rotational movement but also coupled to a linear screw 102b with an actuator generating a longitudinal movement.

The driver unit 3 can be connected to a base unit (not shown). The base unit can provide power and possibly also vacuum and pressurized air to the driver unit 3. Alternatively the driver unit 3 can be connected directly to a power point without the need of a base unit in between. Power is needed both for the suction generating device 101 and the needle moving device 102.

The suction generating device 101 is typically a sealed air connection coupled to a vacuum pump with an integrated back flow valve to ensure air only flows in on direction.

In one embodiment of the invention the driver unit 3 further comprises a pulsing device 103 which can transfer longitudinal, reciprocating pulses to a biopsy needle of a connected probe. Such a reciprocating oscillating movement of the needle or a part of the needle (inner needle part and/or outer needle part, such as cannulas or trocars) is especially suitable when dense or fibrotic tissue need to be penetrated on the way to a tumor. Also when penetrating the tumor for taking a biopsy the oscillating movement can preferably be used in order to improve the filling of the needle with tissue utilizing the inertia stabilization caused by the fast acceleration pulses applied to the needle. The pulsing device 103 can be a piston arrangement. Such a piston arrangement comprises a piston arranged to reciprocate in a piston casing. This piston arrangement is driven by a movement generating source (not shown), e.g. weight accelerated by pressurized air generated by a compressor. Such a movement generating source can be provided either in the driver unit 3 or in a base unit to which the driver unit can be connected. In an alternative, the piston arrangement is driven by magnetic forces, hydraulic forces or spring-generated forces. In another alternative, the piston arrangement is driven by forces generated by an electric motor or a piezo-electric device. In EP 2323563, EP 3206587 and WO 2016/058845 the present applicant describes details of one type of pulsing device which can be used also in this invention.

The driver unit 3 comprises furthermore a first connection device 11 for realeasable connection to said probes 5a, 5b, 5c, 5d. The first connection device 11 can be provided as one or more recesses and/or projecting parts 11 for mating with corresponding recesses/projecting parts 23a, 23b, 23c, 23d on a probe 5a, 5b, 5c, 5d. These recesses and/or projecting parts 11 can be provided to the driver connection surface 9 as shown in FIG. 2b, i.e. in this example two projecting parts 11 in one end of the driver unit and two recesses in an opposite end. However different configurations are of course possible. Furthermore, in this example the first connection device 11 further comprises a front connection device 11a provided in a front end of the driver unit 3 for mating with a front connection device 23a' of a probe. In this example the first connection device 11 furthermore comprises a releasing button 11b. A probe connected to the driver unit 3 can be released by pushing this releasing button 11b. This release button 11b is hereby connected to a locking device provided to the recesses and/or projecting parts 11 of the first connection device 11.

At least one activation button 13a, 13b is provided on an outside surface of the driver unit 3. This activation button 13a, 13b is connected to the at least two different probe controlling devices 101, 102, 103, 104 of the driver unit 3. A physician using the biopsy arrangement 1 can activate the different probe controlling devices by pushing this at least one activation button 13a, 13b. One push on the activation button can in some embodiments initiate a whole sampling sequence and/or a number of pushes on the activation button can activate different steps in a sampling sequence. More than one activation button 13a, 13b could also be provided for initiating different steps of a sampling sequence. In this embodiment two activation buttons 13a, 13b are provided, where a first activation button 13a is for activation of a sampling sequence and/or different steps of a sampling sequence and a second activation button 13b is provided for controlling a pulsing device of the driver unit as described above.

A first probe type 5a is shown in FIGS. 3a and 3b. FIG. 3a is a side view of the first probe type 5a and FIG. 3b is a top view of the first probe type 5a showing a probe connection surface 21a of the first probe type 5a which probe connection surface 21a can be mated and connected with the driver connection surface 9 of the driver unit 3. The first probe type 5a comprises a second connection device 23a for releasable connection to the first connection device 11 of the driver unit 3. The second connection device 23a can be provided as one or more recesses and/or projecting parts for mating with corresponding recesses/projecting parts 11 on a driver unit 3. The recesses and/or projecting parts 23a can be provided to the probe connection surface 21a as shown in FIG. 3b, i.e. in this example two projecting parts 23a in one end of the probe and two recesses 23a in an opposite end. However different configurations are of course possible. Furthermore, in this example the second connection device 23a further comprises a front connection device 23a' provided in a front end of the probe 5a for mating with a front connection device 11a of the driver unit 3. The first probe type 5a comprises at least two different probe modules 201, 202. These probe modules comprise a suction transferring module 201 and at least one needle manipulating module 202. The suction transferring module 201 is configured for transferring suction from the suction generating device 101 of the driver unit 3 to a needle 25a of the first probe 5a. By providing suction to the needle 25a a biopsy sample can be sucked into a sample receiving opening 27a of the needle and the biopsy sample can possibly also be transferred within the needle 25 to a sample collection device 28a possibly provided in the single use probe 5a. Hereby a number of biopsy samples can be taken and transferred through the needle to the sample collection device 28a without the need to remove the needle from the tumor/lesion. However a sample collection device 28a is not necessary for the invention. The at least one needle manipulating module 202 for the first probe type 5a is called a first probe type needle manipulating module 202 and it can be configured for providing longitudinal and/or rotational movement to at least a part of the needle 25a of the first probe type 5a. In one embodiment of the invention, as shown in FIGS. 5a and 5b, both longitudinal and rotational movement is provided to the needle 25. If the needle 25a comprises an inner needle part 29a and an outer needle part 31a (which in this embodiment both are cannulas), i.e. an inner cannula provided inside an outer cannula, the first probe type needle manipulating module 202 can be configured to provide longitudinal movement to only the inner needle part 29a in relation to the outer needle part 31a hereby providing the opening and closing of the sample receiving opening 27a. Furthermore the first probe type needle manipulating module 202 can be configured for providing rotational movement to only the inner needle part 29a in order to cut off the biopsy sample. However, another alternative would be to provide the longitudinal movement and the rotational movement to only the outer needle part 31a for cutting off the biopsy sample. The first probe type needle manipulating module 202 comprises in this embodiment a rotational movement generating part 202a, for example a cogwheel, and a longitudinal movement generating part 202b, for example a linear screw with an actuator. The first probe type needle manipulating module 202 is configured for connecting to the needle moving device 102 of the driver unit 3. In this embodiment of the invention the first probe type 5a further comprises a pulse transferring module 203, which is configured for transferring reciprocating pulses provided from the pulsing device 103 of the driver unit 3 to the biopsy needle 25a of the first probe type 5a when connected to the driver unit 3. This first probe type pulse transferring module 203 can be configured for transferring the reciprocating pulses to only one of the inner or outer needle part 29a, 31a of the needle 25a or to both the inner and outer needle part 29a, 31a. In this first probe type 5a it can be advantageous to only transfer the reciprocating pulses to the outer needle part 31a of the needle 25a.

For the first probe type 5a the whole sampling sequence can in one embodiment be initiated by only one push on a first activation button 13a of the driver unit 3 when the needle has been placed in a position suitable for tissue sampling. Hereby the suction generating device 101 is first activated for generating a vacuum to the needle and then the needle moving device 102 is automatically activated such that the inner needle part 29a is rotated and translated longitudinally in relation to the outer needle part 31a, first back for filling the needle with sample and then forward for severing the sample whereby the sample is transported to the sample collection device 28a due to the pressure difference. A second activation button 13b can be pushed for activating the pulsing device 103 during needle positioning before the sampling process.

A second probe type 5b is shown in FIGS. 4a and 4b. FIG. 4a is a side view of the second probe type 5b and FIG. 4b is a top view of the second probe type 5b showing a probe connection surface 21b of the second probe type 5a which probe connection surface 21b should be mated and connected with the driver connection surface 9. The second probe type comprises a second connection device 23b for releasable connection to the first connection device 11 of the driver unit 3 for example provided as projecting parts and/or recesses 23b and a front connection device 23b' on the probe connection surface 21b in the same way as described above for the first probe type 5a. The second probe type 5b comprises at least one probe module which is a needle manipulating module 204, in this embodiment called a second probe type spring loaded needle manipulating module 204. Said second probe type spring loaded needle manipulating module 204 is configured for providing a spring loaded longitudinal movement to at least a part of a needle 25b of the second probe type 5b. Also this needle 25b can comprise an inner needle part 29b and an outer needle part 31b (which in this embodiment both can be cannulas) whereby a sample receiving opening 27b can be opened or closed by a relative motion between the inner and outer needle part 29b, 31b. The inner needle part 29a can in one embodiment be provided with the sample receiving opening 27b at a side surface of a top part of the needle and the outer needle part 31b can be configured for cutting the sample provided into the opening 27b when the outer needle part 31b is moved in relation to the inner needle part 29b for closing the opening 27b. The longitudinal motion of first the inner needle part 29b into a tumor and thereafter the outer needle part 31b to cut the sample is in this second probe type 5b provided by a spring loaded action. This is what usually is called core needle biopsy. The spring loading is provided in the second probe type spring loaded needle manipulating module 204 which is connected to the needle moving device 102 of the driver unit 3 for being activated. At least one spring is hereby provided in the second probe type spring loaded needle manipulating module 204. For example one spring can be provided for loading only the outer needle part 31b. In another example two springs can be provided for loading the inner needle part 29b and the outer needle part 31b separately. The second probe type spring loaded needle manipulating module 204 is configured for connecting to the needle moving device 102 of the driver unit 3 for loading and releasing the at least one spring. For example a coil spring can be used and loaded to for example 30-60 N in dependence of the weight of the needle part to be accelerated. In one example the outer needle part should be accelerated over a distance between 15-30 mm to a speed of 7-15 m/s.

Also the second probe type 5b can in one embodiment of the invention comprise a pulse transferring module 205, which is configured for transferring reciprocating pulses provided from the pulsing device 103 of the driver unit 3 to the needle 25b of the second probe type 5b when connected to the driver unit 3. This second probe type pulse transferring module 205 can be configured for transferring the reciprocating pulses to only one of the inner or outer needle part 29b, 31b of the needle 25b or to both the inner and outer needle part 29b, 31b. In this second probe type 5b it can be advantageous to transfer the reciprocating pulses to both the inner and outer needle parts 29b, 31b of the needle 25b.

For the second probe type 5b the sampling sequence can in one embodiment be initiated by a first push on a first activation button 13a of the driver unit 3 when the needle has been placed in a position suitable for tissue sampling. The first push on the first activation button 13a will activate the needle moving device 102 such that an outer needle part 31b of the needle will be retracted, a spring will be loaded and tissue will fill the sample receiving opening 27b. A second push on the first activation button 13a will release the spring whereby the outer needle part 31b will move forward and hereby close the sample receiving opening 27b of the needle and a sample will be severed. A second activation button 13b can be pushed for activating the pulsing device 103 during needle positioning before the sampling process.

A third probe type 5c is shown in FIGS. 5a and 5b. FIG. 5a is a side view of the third probe type 5c and FIG. 5b is a top view of the third probe type 5c showing a probe connection surface 21c of the third probe type 5c which probe connection surface 21c should be mated and connected with the driver connection surface 9. The third probe type comprises a second connection device 23c for releasable connection to the first connection device 11 of the driver unit 3 for example provided as projecting parts and/or recesses 23c and a front connection device 23c' on the probe connection surface 21c in the same way as described above for the first probe type 5a. The third probe type 5c comprises at least two probe modules.

The third probe type 5c is a different type of probe than the first and the second probe types. Probe modules of the third probe type 5c comprise a suction transferring module 206, a needle manipulating module 207, in this embodiment called a third probe type needle manipulating module 207 and possibly also a pulse transferring module 208. Said suction transferring module 206 is configured for transferring a suction from the suction generating device 101 of the driver unit 3 to a needle 25c of the third probe type 5c. Said third probe type needle manipulating module 207 is configured for providing longitudinal movement to an inner needle part 29c of the needle 25c of the third probe type 5c for positioning of the inner needle part 29c in a front or back position in relation to an outer needle part 31c of the needle 25c. Said pulse transferring module 208 is configured for transferring reciprocating pulses provided from the pulsing device 103 of the driver unit 3 to the inner and/or outer needle part 29c, 31c of the needle 25c of the third probe type 5c. In one embodiment of the invention a needle part connection device is provided in connection with the pulse transferring module 208, which needle part connection device is configured for keeping the inner and outer needle part together or separated such that the pulses can be provided either to the combined unit of inner and outer needle part of the needle or to one of them separately. One example of such a pulse transferring module and needle part connection device is described by the present applicant in EP 3206587 and WO 2016/058845.

The third probe type comprises furthermore in this embodiment, but not necessarily a sample separating module 209. The sample separating module 209 is configured to be connected to a sample separating device 104 (seen in FIG. 2b) optionally provided in the driver unit 3 when the third probe is connected to the driver unit. The sample separating module 209 and sample separating device 104 are however not necessary for the invention. The sample separating device 104, provided in the driver unit 3 can be a cogwheel connected to a motor and the sample separating module 209 provided in the probe can be a cogwheel connected to an outer needle part 31c of the needle 25c such that a rotational movement can be provided to the outer needle part 31c in order to separate a sample, i.e. cut a sample from the tissue. By providing two separate motors in the driver unit 3, where one motor is for providing longitudinal movement to the needle and one motor is provided for separating a sample by rotating a part of the needle, a rotation can be provided to a part of the needle independently of a longitudinal movement of the needle which is advantageous with this type of sample severing method. Furthermore, when different motors are provided for these two separate functions different motor performances can be used for the different motors, which is suitable. A fast rotation with a high starting torque is suitable for the sample severing process. This is also described in more detail in EP 3206587 and WO 2016/058845.

For the third probe type 5c the sampling sequence can in one embodiment be initiated by a first push on a first activation button 13a of the driver unit 3 when the needle has been placed in a position suitable for tissue sampling. The first push will in one embodiment activate the needle moving device 102 such that the inner needle part 29c is retracted and also activate the suction generating device 101. In this position the second activation button 13b can be used for activating the pulsing device 103. Hereby the needle can be pulsed into the lesion and sample will fill the needle. Thereafter a second push of the first activation button 13a will activate the sample separation device 104 and a sample will be severed as described above. After having removed the needle from the patient a third push of the first activation button 13a can then activate the needle moving device 102 again such that the inner needle part 29c is moved forward and the sample hereby is pushed out from the needle. In this embodiment the inner needle part can be a solid trocar and the outer needle part a cannula.

A fourth probe type 5d is shown in FIGS. 6a and 6b. FIG. 6a is a side view of the fourth probe type 5d and FIG. 6b is a top view of the fourth probe type 5d showing a probe connection surface 21d of the fourth probe type 5d which probe connection surface 21d should be mated and connected with the driver connection surface 9. The fourth probe type comprises a second connection device 23d for releasable connection to the first connection device 11 of the driver unit 3 for example provided as projecting parts and/or recesses 23d and a front connection device 23d' on the probe connection surface 21d in the same way as described above for the first probe type 5a. The fourth probe type 5d is similar to the second probe type 5b and comprises a needle manipulating module 204', which is spring loaded in the same way as described above in relation to the second probe type 5b. The fourth probe type 5d can suitably also comprise a pulse transferring module 205', which is configured for transferring reciprocating pulses provided from the pulsing device 103 of the driver unit 3 to a needle 25d of the fourth probe type 5d when connected to the driver unit 3. The needle 25d of the fourth probe type 5d comprises an inner needle part 29d and an outer needle part 31d, where the inner needle part 29d is arranged to push out a marker 32 in the tissue when the needle 25d has been positioned correctly in the tissue. The longitudinal movement of the inner needle part 29d for pushing out the marker 32 is controlled by the needle manipulating module 204'. In this embodiment the inner needle part can be a solid trocar and the outer needle part can be a cannula. The outer needle part 31d is suitably provided with a sharp beveled end for penetrating the tissue.

As a complement or alternative any one of the first, second or third probe types 5a, 5b, 5c can comprise a further probe module (not shown) for leaving a marker in a human or animal tissue, i.e. a marker function could be integrated in the first, second and/or third probe types 5a, 5b, 5c.

The needles 25a, 25b, 25c, 25d of the different probe types 5a, 5b, 5c, 5d can as described above comprise an inner and an outer needle part 29a, b, c, d, 31a, b, c, d. The sampling method can be either a distal-tip sampling method as shown for the third probe type 5c or a side aperture sampling method as shown for the first and second probe types 5a, 5b.

Each one of the different single use probe types 5a, 5b, 5c, 5d comprises according to one embodiment of the invention a unique probe identification 41a, 41b, 41c, 41d and the reusable drive unit 3 comprises a probe identification recognition device 43. The probe identification and the probe identification recognition device can be based on for example mechanical activation or electrical or optical reading. In the embodiments as shown in FIGS. 2-6 the probe identification is provided as projections provided in different patterns 41a, 41b, 41c, 41d on the connection surface 21a, 21b, 21c, 21d of the probes 5a, 5b, 5c, 5d. These projections are received in corresponding recesses with sensors 43 (probe identification recognition device) in the connection surface 9 of the driver unit 3. The probe identification recognition device 43 of the driver unit 3 is connected to the at least two different probe controlling devices 101, 102, 103, 104 and comprises control logic such that the probe identification recognition device 43 can activate certain probe controlling devices 101, 102, 103, 104 in dependence of which type of probe 5a, 5b, 5c, 5d has been identified by the probe identification recognition device 43. The control logic can be a microprocessor with software connected to position indicators. Other identification methods such as for example RFID are of course possible and covered by the invention.

Other types of probes which can be connected to the driver unit according to the invention than those described above with reference to the drawings 3, 4, 5 and 6 can also be provided. Probe modules can be chosen from the ones described above and be combined in different ways and further probe modules can be provided. Furthermore a design of the needle of the probe can be varied, for example either a distal-tip or a side aperture sampling method can be provided.

The invention claimed is:
1. A biopsy arrangement for taking a biopsy in a human or animal tissue, said biopsy arrangement comprising:
   a driver unit; and
   a plurality of probe types each configured to be releasably connected to the driver unit, wherein the plurality of probe types includes a first probe type and a second probe type, wherein the first probe type includes a first probe module and a second probe module, wherein the second probe type includes a third probe module,
   wherein said driver unit comprises a plurality of different probe controlling devices, wherein the plurality of different probe controlling devices are configured to control the first probe module and the second probe module when the first probe type is connected to the driver unit, wherein the plurality of different probe controlling devices are configured to control the third probe module when the second probe type is connected to the driver unit, wherein the plurality of different probe controlling devices includes a suction generating device and a needle moving device, and wherein the first probe type further includes a first needle, wherein the first probe module is a suction transferring module and the second probe module is a first probe type needle manipulating module, wherein said suction transferring module is configured for transferring a suction from the suction generating device of the driver unit to the first needle of the first probe type, and wherein said first probe type needle manipulating module is configured for providing longitudinal and/or rotational movement to at least a part of the first needle of the first probe type, and wherein the second probe type further includes a second needle, wherein the third probe module is a second probe type spring loaded needle manipulating module which is configured for providing a spring loaded longitudinal movement to at least a part of the second needle of the second probe type, wherein by the first probe type having the first probe module and the second probe module, and the second probe type having the third probe module, the first and second probe types are configured for different sampling techniques, whereby both core needle biopsy and vacuum assisted biopsy can be provided by one and the same biopsy arrangement, wherein said plurality of probe controlling devices of the driver unit further includes a pulsing device configured to provide reciprocating pulses, wherein the first probe type and the second probe type include respectively a first probe type pulse transferring module and a second probe type pulse transferring module, wherein either:

the first probe type pulse transferring module is configured for transferring the reciprocating pulses provided from the pulsing device of the driver unit to both an inner and an outer needle part of the first needle when the first probe type is connected to the driver unit and the second probe type pulse transferring module is configured for transferring the reciprocating pulses provided from the pulsing device of the driver unit to only one of an inner and an outer needle part of the second needle when the second probe type is connected to the driver unit, or the second probe type pulse transferring module is configured for transferring the reciprocating pulses provided from the pulsing device of the driver unit to both the inner and the outer needle part of the second needle when the second probe type is connected to the driver unit and the first probe type pulse transferring module is configured for transferring the reciprocating pulses provided from the pulsing device of the driver unit to only one of the inner and the outer needle part of the first needle when the first probe type is connected to the driver unit.

2. A biopsy arrangement according to claim 1, wherein said plurality of probe types includes a third probe type including a third needle and a second suction transferring module, and wherein said suction generating device of the driver unit is further configured for connecting to the second suction transferring module when the third probe type is connected to the driver unit, wherein the third probe type further includes a third probe type needle manipulating module, and wherein said needle moving device of the driver unit is configured for connecting to said third probe type needle manipulating module when the third probe type is connected to the driver unit for controlling longitudinal and/or rotational movement of at least a part of the third needle of the third probe type.

3. A biopsy arrangement according to claim 1, wherein said plurality of probe types further includes a third probe type including a third needle, a second suction transferring module, and a third probe type needle manipulating module, and wherein said second suction transferring module is configured for transferring the suction from the suction generating device of the driver unit to the third needle of the third probe type when the third probe type is connected to the driver unit, and wherein said third needle manipulating module is configured to provide longitudinal movement to an inner needle part of the third needle for positioning of the inner needle part in a front or back position in relation to an outer needle part of the third needle and configured to provide rotational movement to the outer needle part of the third needle.

4. A biopsy arrangement according to claim 3, wherein the plurality of different probe controlling devices includes a sample separating device comprising or being connected to a motor in the driver unit, wherein said third probe type further includes a sample separating module configured for cooperating with said sample separating device when the third probe type is connected to the driver unit, wherein said sample separating module is connected to the outer needle part of the third needle such that a second rotational movement can be provided to the outer needle part from the sample separating device through the sample separating module.

5. A biopsy arrangement according to claim 3, wherein said third probe type further includes a third probe type pulse transferring module configured to transfer reciprocating pulses provided from the pulsing device of the driver unit to the inner and/or the outer needle part of the third needle when the third probe type is connected to the driver unit.

6. A biopsy arrangement according to claim 1, wherein the plurality of probe types further comprises a third probe type, wherein said third probe type is a marker probe configured to leave a marker in the human or animal tissue.

7. A biopsy arrangement according to claim 1, wherein said plurality of probe types further includes a third probe type including a third needle, wherein the third needle of the third probe type comprises a distal-tip loaded needle and at least one of the first needle of the first probe type or the second needle of the second probe type comprises a side aperture needle.

8. A biopsy arrangement according to claim 1, wherein each probe type of the plurality of probe types includes a unique probe identification and the driver unit includes a probe identification recognition device which includes control logic such that the probe identification recognition device activates one or more of the plurality of different probe controlling devices based on the probe type identified by the probe identification recognition device.

9. A biopsy arrangement according to claim 1, wherein the first probe type includes a sample collection device connected to the first needle.

* * * * *